United States Patent [19]

Zaiger et al.

[11] Patent Number: Plant 7,432

[45] Date of Patent: Jan. 29, 1991

[54] PEACH TREE (RICH MAY)

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 462,091

[22] Filed: Jan. 8, 1990

[51] Int. Cl.[5] ..... A01H 5/00

[52] U.S. Cl. ..... Plt./43

[58] Field of Search ..... Plt./43

*Primary Examiner*—James R. Feyrer

[57] ABSTRACT

A new and distinct variety of peach tree; its novelty consisting of the following unique combination of desirable features.

1. Early maturity of fruit.
2. Producing large size, yellow flesh fruit.
3. Heavy and regular production.
4. The ability of the fruit to stay firm 4–5 days after maturity.
5. Vigorous upright growth habit.
6. Producing firm fruit with good handling and shipping quality.

1 Drawing Sheet

ORIGIN OF THE VARIETY

The present variety of peach tree was originated by us in the experimental orchard located near Modesto, Calif. as a cross between two selected seedlings with the field identification numbers 34GA1155×36EB346. The female parent 34GA1155 was a cross between a selected seedling from a May Grand Nectarine (U.S. Plant Pat. No. 2,794) crossed with a peach of unknown parentage. This selection was then crossed with an open pollinated seedling of Sam Houston Peach (non-patented). The pollen parent 36EB346 originated from a first generation cross of Tasty Gold Nectarine (U.S. Plant Pat. No. 5,623) crossed with May Crest Peach (U.S. Plant Pat. No. 4,064).

ASEXUAL REPRODUCTION OF THE VARIETY

The new and distinct variety of peach tree was asexually reproduced by budding as preformed by us in the experimental orchard located near Modesto, Calif. and shows that said characteristics come true to the original tree and are established and transmitted through succeeding propagations.

SUMMARY OF THE VARIETY

Our new and distinct variety of peach tree is of large size, vigorous upright in growth, a regular and productive bearer of large size, yellow flesh, clingstone fruit with good flavor and eating quality. The fruit is further characterized by holding firm on the tree 4 to 5 days after maturity, having yellow ground color overspread with an attractive red blush, firm flesh with good storage and shipping quality. The present variety of peach tree is further characterized by maturing fruit 4 to 5 days before May Crest Peach (U.S. Pat. No. 4,064), with heavier production of larger size fruit.

BRIEF DESCRIPTION OF THE PHOTOGRAPHS

The accompanying photographs show reproductions in color of typical specimens of the fruit and foliage of the new variety of peach tree. The upper and lower surface of the leaves being illustrated and a fruit being divided in the suture plane to reveal flesh coloration and showing a stone remaining in place. The photographs of the fruit were taken shortly after being picked (firm ripe) and the colors are as nearly true as is reasonably possible in a color presentation of this type.

DESCRIPTION OF THE VARIETY

The following is a botanical description of the peach tree and its flowers, foliage and fruit as based on observations of the specimens grown near modesto, Calif., with color terminology (except those in common terms) in accordance with Reinhold color atlas by A. Korneruf and J. H. Wanscher.

Tree:
- *Size.*—Large.
- *Vigor.*—Vigorous.
- *Form.*—Upright.
- *Density.*—Medium dense.
- *Shape.*—Normally pruned to vase shape.
- *Production.*—Productive.
- *Bearer.*—Regular.

Trunk:
- *Size.*—Medium stocky.
- *Texture.*—Medium shaggy.
- *Color.*—Brown to light brown (5-E-6) to (5-E-8).

Branches:
- *Size.*—Medium to large.
- *Texture.*—Smooth to medium rough.
- *Lenticels.*—Numerous. Large size.
- *Color.*—Brown to reddish brown.

Leaves:
- *Size.*—Medium to large. Average length — 6" to 6½". Average width — 1¼" to 1 ½".
- *Form.*—Mostly lanceolate, some oblanceolate.
- *Texture.*—Smooth.
- *Margin.*—Crenate.
- *Thickness.*—Medium.
- *Petiole.*—Medium length. Medium thickness.
- *Color.*—Upper surface — green to deep green (28-F-7) to (28F-8). Lower surface — green to dull green (29-E-7) to (29-E-8).
- *Glands.*—Reniform. Medium size. Numbers varies from 1 to 3. Average number 2. Positioned on base of leaf and upper portion of petiole.

Flower buds:

*Size.*—Medium.
*Form.*—Plump.
*Pubescence.*—Pubescent.

Flowers:
*Size.*—Large — showy.
*Blooming period.*—Mar. 1, 1988 to Mar. 9, 1988. Varies slightly with climatic conditions.
*Pollen.*—Present.
*Color.*—Pink.

Fruit:
*Maturity when described.*—Firm ripe.
*Date of first picking.*—May 14, 1988.
*Date of last picking.*—May 19, 1988.
*Size.*—Large. Average diameter axially — 2 ¾" to 3". Average transversely in suture plane — 2 ½" to 2μ".
*Form.*—Nearly globose — slightly elongated in suture plane.
*Suture.*—Shallow — nearly smooth, extends from base to apex.
*Cavity.*—Rounded to very slightly elongated in suture plane. Average depth — 7/16" Average breadth — ⅞".
*Base.*—Retuse.
*Apex.*—Usually round, some fruit with very slight point.

Skin:
*Thickness.*—Medium.
*Texture.*—Medium.
*Tendency to crack.*—None.
*Down.*—Moderate. Medium length.
*Color.*—Yellow ground color — (4-A-5) to (4-A-7). Overspread with liquid red blush — (8-A-8) to (9-B-8).

Flesh:
*Ripens.*—Even.
*Texture.*—Firm.
*Fibers.*—Few — tender.
*Flavor.*—Mild — good balance between acid and sugar.
*Eating quality.*—Good.
*Color.*—Light yellow to yellow — (4-A-5) to (4-A-7).

Stone
*Type.*—Clingstone.
*Size.*—Large. Average length — 1⅜". Average breadth — 1 1/16". Average thickness — ¾".
*Form.*—Ovid.
*Base.*—Mostly straight.
*Apex.*—Accute.
*Sides.*—Nearly equal.
*Surface.*—Furrowed toward apex — pitted throughout, heavier toward base.
*Tendency to split.*—Slight.
*Color.*—Tan to light brown — (7-C-5) to (7-D-5).

Use: Dessert.
*Market.*—Local and long distance.

Keeping quality: Good.
Shipping quality: Good.

The present variety of peach tree, its fruit and foliage herein described may vary in slight detail due to climatic, soil conditions and cultural practices under which the variety may be grown; the present description being of the variety grown by use under the ecological conditions prevailing at Modesto, Calif.

We claim:

1. A new and distinct variety of peach tree as illustrated and described, characterized by its large size, vigorous upright growth and a regular and productive bearer of large size early maturing, yellow flesh, clingstone fruit with good eating, shipping and storage quality; the fruit is further characterized in comparison to the variety May Crest Peach (U.S. Plant Pat. No. 4,064) as maturing 4 to 5 days earlier with heavier production of larger size fruit.

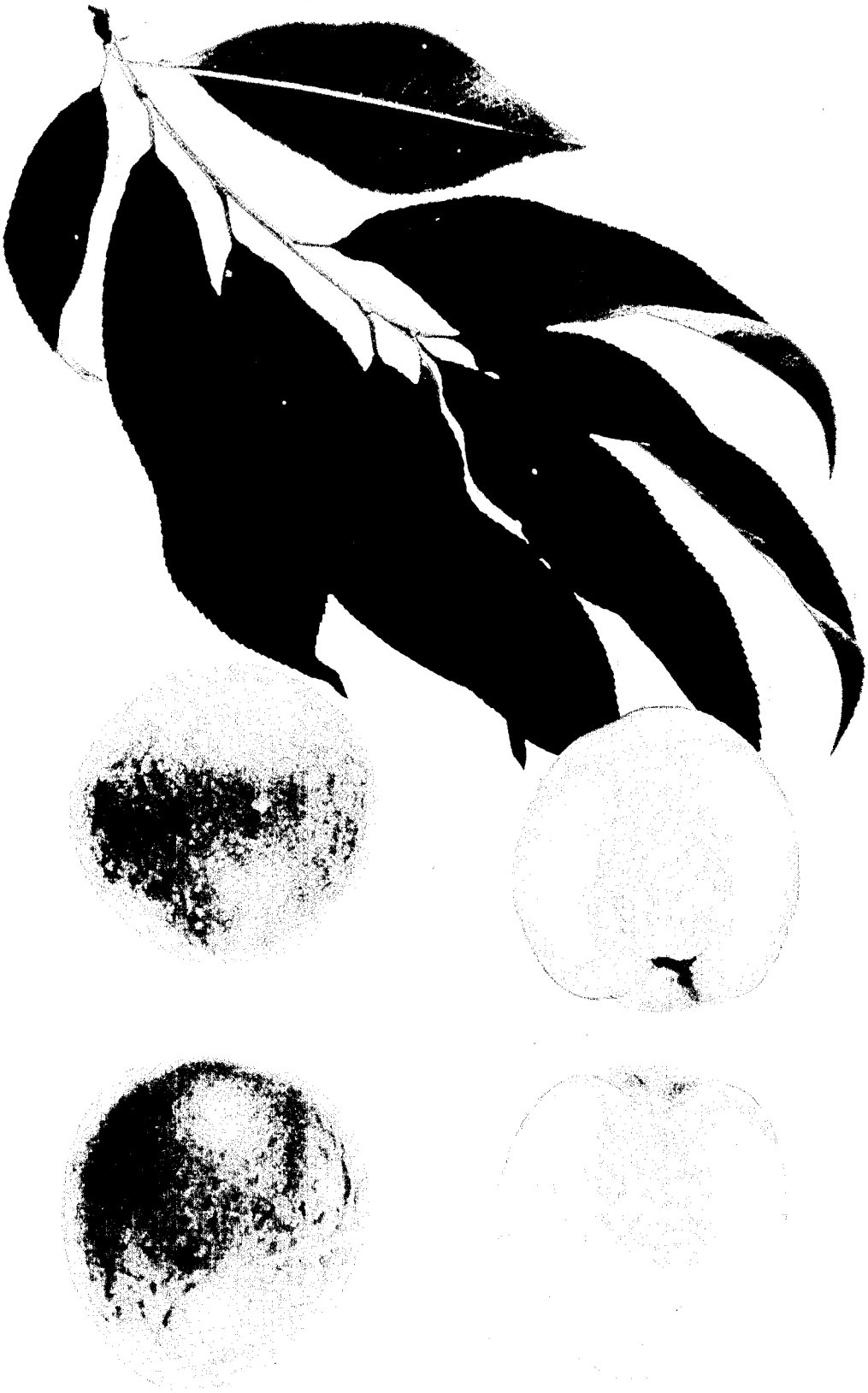

* * * * *